United States Patent [19]

Jahn et al.

[11] Patent Number: 4,612,036
[45] Date of Patent: Sep. 16, 1986

[54] CYCLOHEXANE-1,3-DIONE DERIVATIVES AND THEIR USE FOR CONTROLLING UNDESIRABLE PLANT GROWTH

[75] Inventors: Dieter Jahn, Edingen-Neckarhausen; Rainer Becker, Bad Durkheim; Michael Keil, Freinsheim; Bruno Wuerzer, Otterstadt, all of Fed. Rep. of Germany

[73] Assignee: BASF Aktiengesellschaft, Ludwigshafen, Fed. Rep. of Germany

[21] Appl. No.: 750,997

[22] Filed: Jul. 2, 1985

Related U.S. Application Data

[63] Continuation of Ser. No. 573,617, Jan. 25, 1984, abandoned.

[30] Foreign Application Priority Data

Feb. 1, 1983 [DE] Fed. Rep. of Germany ....... 3303182

[51] Int. Cl.⁴ ................. A01N 43/10; A01N 43/18; C07D 333/48; C07D 335/02
[52] U.S. Cl. .......................... 71/91; 549/9; 549/11; 549/21; 549/28; 549/37; 549/39; 549/65; 549/75; 549/88; 549/89
[58] Field of Search ............... 549/9, 11, 21, 28, 37, 549/39, 65, 75, 88, 89; 71/91

[56] References Cited

U.S. PATENT DOCUMENTS

| 3,297,718 | 1/1967 | Sander .................... 71/91 X |
| 3,454,391 | 7/1969 | von Schmeling et al. ......... 71/91 X |
| 4,422,864 | 12/1983 | Becker et al. ............... 71/88 |

FOREIGN PATENT DOCUMENTS 1461170  1/1977  United Kingdom .

*Primary Examiner*—Richard L. Raymond
*Attorney, Agent, or Firm*—Keil & Weinkauf

[57] ABSTRACT

Cyclohexane-1,3-dione derivatives of the formula

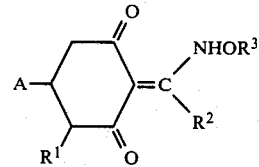

where A is an unsubstituted or substituted, saturated or unsaturated 4-membered to 7-membered ring which contains 1 or 2 sulfinyl or sulfonyl groups, $R^1$ is hydrogen, methoxycarbonyl, ethoxycarbonyl, methyl or cyano, $R^2$ is alkyl and $R^3$ is alkyl, alkenyl, haloalkenyl or propargyl, and salts of these compounds are used for controlling undesirable plant growth.

11 Claims, No Drawings

CYCLOHEXANE-1,3-DIONE DERIVATIVES AND THEIR USE FOR CONTROLLING UNDESIRABLE PLANT GROWTH

This application is a continuation of application Ser. No. 573,617 filed on Jan. 25, 1984, abandoned.

The present invention relates to cyclohexane-1,3-dione derivatives and herbicides which contain these compounds as active ingredients.

It is known that cyclohexane-1,3-dione derivatives can be used for controlling undesirable grasses in broad-leaved crops (German Laid-Open Application DOS No. 2,439,104).

We have found that cyclohexane-1,3-dione derivatives of the formula

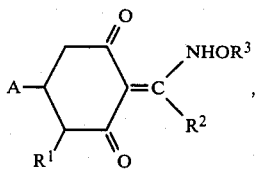

where A is a saturated or unsaturated 4-membered to 7-membered ring which contains 1 or 2 sulfinyl or sulfonyl groups and is unsubstituted or substituted by not more than 3 alkyl groups, each of not more than 4 carbon atoms, 2 alkenyl groups, each of not more than 6 carbon atoms, or 3 alkoxy groups, each of not more than 2 carbon atoms, $R^1$ is hydrogen, methoxycarbonyl, ethoxycarbonyl, methyl or cyano, $R^2$ is alkyl of 1 to 4 carbon atoms and $R^3$ is alkyl of 1 to 4 carbon atoms, alkenyl of 3 or 4 carbon atoms or haloalkenyl of 3 or 4 carbon atoms which has 1 to 3 halogen substituents, or is propargyl, and salts of these compounds, have a herbicidal action against grasses and are selective both in broad-leaved crops and in monocotyledon crops which do not belong to the family of the grasses (Gramineae).

The compounds of the formula I can occur in several forms, all of which are embraced by the patent claim:

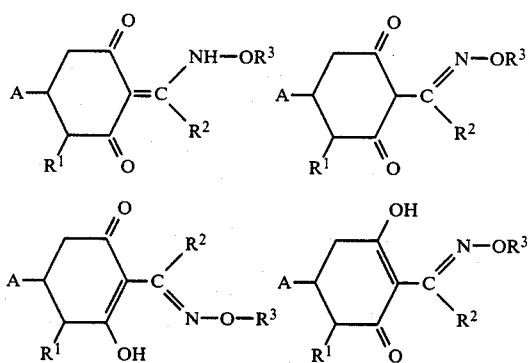

In formula I, A is a saturated or unsaturated 4-membered to 7-membered, preferably 5-membered or 6-membered, ring which contains 1 or 2 sulfinyl or sulfonyl groups and is unsubstituted or substituted by not more than 3 alkyl groups, each of not more than 4 carbon atoms, 2 alkenyl groups, each of not more than 6 carbon atoms, or 3 alkoxy groups, each of not more than 2 carbon atoms, the substituents being identical or different. Examples of A are 1-oxotetrahydrothiopyranyl, 1,1-dioxotetrahydrothiopyranyl, 5,6-dihydro-2H-1-oxothiopyranyl, 5,6-dihydro-2H-1,1-dioxothiopyranyl, 1-oxotetrahydrothienyl, 1,1-dioxotetrahydrothienyl, 5,6-dihydro-1-oxothienyl and 5,6-dihydro-1,1-dioxothienyl, which are substituted by alkyl of not more than 4 carbon atoms, for example by methyl, ethyl or i-propyl, preferably by methyl, by alkenyl of 1 to 6 carbon atoms, for example by allyl, but-2-enyl or 3-methylbut-2-enyl, or by alkoxy of not more than 2 carbon atoms, ie. by methoxy or ethoxy, eg. 1-oxotetrahydrothiopyran-3-yl, 1,1-dioxotetrahydrothiopyran-3-yl, 5,6-dihydro-2H-1-oxothiopyran-3-yl, 5,6-dihydro-2H-1,1-dioxothiopyran-3-yl, 2,6-dimethyl-1-oxo-tetrahydrothiopyran-3-yl, 2,6-dimethyl-1,1-dioxotetrahydrothiopyran-3-yl, 2,6-dimethyl-5,6-dihydro-2H-1-oxothiopyran-3-yl, 2,6-dimethyl-5,6-dihydro-2H-1,1-dioxothiopyran-3-yl, 6-methyl-1-oxotetrahydropyran-3-yl, 6-methyl-1,1-dioxotetrahydropyran-3-yl, 6-methyl-5,6-dihydro-2H-1-oxothiopyran-3-yl, 6-methyl-5,6-dihydro-2H-1,1-dioxothiopyran-3-yl, 1-oxotetrahydrothien-3-yl, 1,1-dioxotetrahydrothien-3-yl, 2,5-dihydro-1-oxothien-3-yl, 2,5-dihydro-1,1-dioxothien-3-yl, 2-methyl-1-oxotetrahydrothien-3-yl, 2-methyl-1,1-dioxotetrahydrothien-3-yl, 2,5-dihydro-2-methyl-1-oxothien-3-yl, 2,5-dihydro-2-methyl-1,1-dioxothien-3-yl, 2,2-dimethyl-1-oxotetrahydrothien-3-yl, 2,2-dimethyl-1,1-dioxotetrahydrothien-3-yl, 2,5-dihydro-2,2-dimethyl-1-oxothien-3-yl, 2,5-dihydro-2,2-dimethyl-1,1-dioxothien-3-yl, 2-methyl-2-(3-methyl-2-buten-1-yl)-1-oxotetrahydrothien-3-yl, 1,1-dioxo-2-methyl-2-(3-methyl-2-buten-1-yl)-tetrahydrothien-3-yl, 2,5-dihydro-2-methyl-2-(3-methyl-2-buten-1-yl)-thien-3-yl, 2,5-dihydro-1,1-dioxo-2-methyl-2-(3-methyl-2-buten-1-yl)-thien-3-yl, 4-methyl-1-oxotetrahydrothien-2-yl, 1,1-dioxo-4-methyltetrahydrothien-2-yl, 2,5-dihydro-4-methyl-1-oxothien-2-yl, 2,5-dihydro-1,1-dioxo-4-methylthien-2-yl, 1-oxotetrahydrothien-2-yl, 1,1-dioxotetrahydrothien-2-yl, 2-methyl-1-oxo-1,3-dithiolan-2-yl, 1,3-dioxo-2-methyl-1,3-dithiolan-2-yl, 2-methyl-1,1,3-trioxo-1,3-dithiolan-2-yl and 2-methyl-1,1,3,3-tetraoxo-1,3-dithiolan-2-yl.

In formula I, $R^2$ is straight-chain or branched alkyl of 1 to 4 carbon atoms, ie. methyl, ethyl, n-propyl, i-propyl, n-butyl, sec.-butyl, i-butyl or tert.-butyl, and $R^3$ is propargyl, alkyl of 1 to 4 carbon atoms, alkenyl of 3 or 4 carbon atoms or haloalkenyl of 3 or 4 carbon atoms which can contain not more than three halogen substituents, eg. methyl, ethyl, n-propyl, i-propyl, n-butyl, sec.-butyl, i-butyl, tert.-butyl, allyl, 1-chloroprop-1-en-3-yl, 2-chloroprop-1-en-3-yl, 1,3-dichloroprop-1-en-3-yl or 1,1,2-trichloroprop-1-en-3-yl.

Preferred cyclohexane-1,3-dione derivatives are compounds of the formula I where $R^1$ is hydrogen. Other preferred compounds of the formula I are those in which A is a 5-membered or 6-membered ring, eg. a 5,6-dihydro-2H-1-oxothiopyranyl radical, in particular 5,6-dihydro-2H-1-oxothiopyran-3-yl, a 1-oxotetrahydrothiopyranyl radical, in particular 1-oxotetrahydrothiopyran-3-yl, or a 1,1-dioxotetrahydropyranyl radical, in particular 1,1-dioxotetrahydropyran-3-yl.

Examples of suitable salts of compounds of the formula I are the alkali metal salts, in particular the potassium or sodium salts, alkaline earth metal salts, in particular the calcium, magnesium or barium salts, manganese salts, copper salts, zinc salts and iron salts, as well as ammonium, phosphonium, sulfonium and sulfoxonium salts, eg. ammonium, tetraalkylammonium, benzyltrialkylammonium, trialkylsulfonium and trialkylsulfoxonium salts.

The compounds of the formula I can be obtained by reacting a compound of the formula

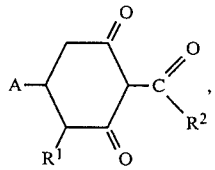

where A, $R^1$ and $R^2$ have the above meanings, with an ammonium compound of the formula $R^3O-NH_3Y$, where $R^3$ has the above meanings and Y is an anion.

The reaction is advantageously carried out in the heterogeneous phase in an inert diluent at from 0° to 80° C., or from 0° C. to the boiling point of the reaction mixture, in the presence of a base. Examples of suitable bases are carbonates, bicarbonates, acetates, alcoholates, hydroxides or oxides of alkali metals or alkaline earth metals, in particular of sodium, potassium, magnesium and calcium. It is also possible to use organic bases, such as pyridine or tertiary amines.

The reaction proceeds particularly well at a pH of from 2 to 9, and the pH is advantageously adjusted by adding an acetate, for example an alkali metal acetate, in particular sodium acetate or potassium acetate, or a mixture of these. Alkali metal acetates are added in amounts of, for example, from 0.5 to 2 moles, based on the ammonium compound of the formula $R_3O-NH_3Y$.

Examples of suitable solvents are dimethyl sulfoxide, alcohols, such as methanol, ethanol or isopropanol, benzene, toluene, hydrocarbons and chlorohydrocarbons, such as chloroform, dichloroethane, hexane or cyclohexane, esters, such as ethyl acetate, and ethers, such as dioxane or tetrahydrofuran.

The reaction is complete after a few hours, and the product can then be isolated by evaporating down the mixture, adding water, extracting with a non-polar solvent, such as methylene chloride, and distilling off the solvent under reduced pressure.

The compounds of the formula I can also be obtained by reacting a compound of the formula II with a hydroxylamine of the formula $R_3O-NH_2$, in which $R^3$ has the above meanings, in an inert diluent at from 0° C. to the boiling point of the reaction mixture, in particular from 15° to 70° C. If desired, the hydroxylamine can be used in the form of an aqueous solution.

Examples of suitable solvents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

The alkali metal salts of the compounds of the formula I can be obtained by treating these compounds with sodium hydroxide or potassium hydroxide in aqueous solution or in an organic solvent, eg. methanol, ethanol, acetone or toluene. Instead of the hydroxides, sodium alcoholates and potassium alcoholates can also be used for the preparation of the alkali metal salts.

The remaining metal salts, eg. the manganese, copper, zinc, iron, calcium, magnesium and barium salts, can be prepared from the sodium salts by reaction with the corresponding metal chloride in aqueous solution. Ammonium, phosphonium, sulfonium or sulfoxonium salts can be obtained by reacting a compound of the formula I with an ammonium, phosphonium, sulfonium or sulfoxonium hydroxide, if necessary in aqueous solution.

The compounds of the formula II can be prepared by a conventional method (Tetrahedron Lett. 29 (1975), 2491) from cyclohexane-1,3-diones of the formula III, which can also occur in the tautomeric forms of the formulae IIIa and IIIb

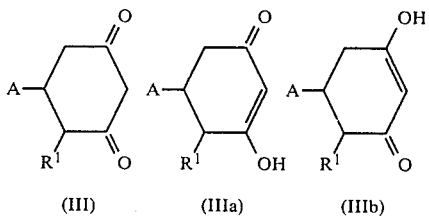

It is also possible to prepare compounds of the formula II via the enol-ester intermediates, which are obtained, possibly as an isomer mixture, in the conversion of a compound of the formula II, and undergo rearrangement in the presence of an imidazole or pyridine derivative (Japanese Preliminary Published Application No. 79/063,052).

The compounds of the formula III are obtained by conventional methods, as can be seen from the diagram below:

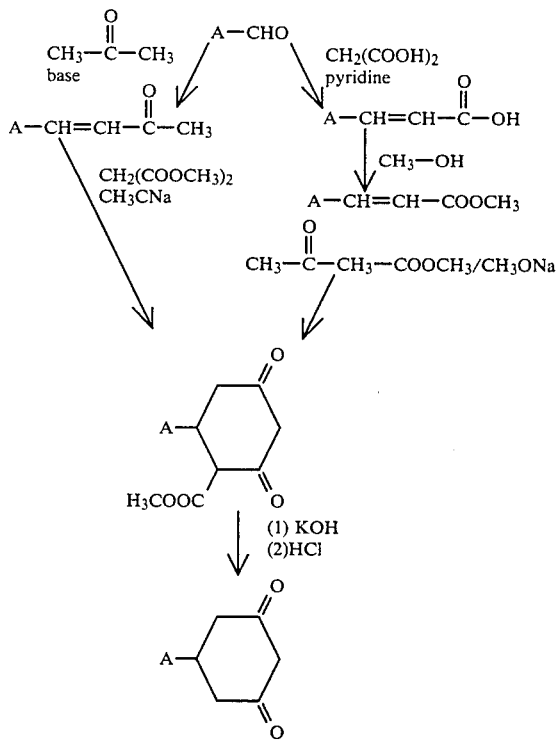

The compounds of the formula I can also be obtained by oxidation of an appropriate precursor in which the sulfur has a lower oxidation state. Examples of oxidizing agents are oxygen, ozone, peroxy compounds, such as hydrogen peroxide, peracids or hydroperoxides, halogens, inorganic halogen compounds, such as hypochlorites or chlorates, nitrogen compounds, such as nitric acid or nitrogen pentoxide, and salts of metals of relatively high valency, such as lead, bismuth, vanadium, manganese, chromium or cobalt salts. Anodic oxidation is also possible. Oxidation can be effected not only at the oxime-ether stage, but in principle at any stage of the synthesis route described above.

The Examples which follow illustrate the preparation of the cyclohexane-1,3-dione derivatives of the formula I. Parts by weight bear the same relation to parts by volume as that of the kilogram to the liter.

EXAMPLE 1

4.7 parts by weight of 2-butyryl-5-(5,6-dihydro-2H-1,1-dioxothiopyran-3-yl)-cyclohexane-1,3-dione, 1.6 parts by weight of ethoxyammonium chloride, 1.4 parts by weight of sodium bicarbonate and 50 parts by volume of methanol were stirred at room temperature for 16 hours. The solvent was distilled off under reduced pressure, 50 parts by volume of water and 50 parts by volume of dichloromethane were added to the residue, and the mixture was stirred, after which the phases were separated, the aqueous phase was extracted with 30 parts by volume of dichloromethane, the combined organic phases were washed with 1N hydrochloric acid and water and dried over sodium sulfate, and the solvent was distilled off under reduced pressure. 2-(Ethoxyaminobutylidene)-5-(5,6-dihydro-2H-1,1-dioxothiopyran-3-yl)-cyclohexane-1,3-dione of melting point 147°–149° C. was obtained (active ingredient no. 1).

EXAMPLE 2

11.9 parts by weight of 2-(ethoxyaminobutylidene)-5-(5,6-dihydro-2H-thiopyran-3-yl)-cyclohexane-1,3-dione were dissolved in 200 parts by volume of chloroform. A solution of 14.9 parts by weight of 85% strength m-chlorobenzoic acid was added dropwise to this solution at 5° C., and a precipitate gradually formed. The reaction mixture was heated to room temperature in the course of 2 hours, the precipitate was filtered off under suction, the solution was extracted with semisaturated sodium bicarbonate solution and dried over sodium sulfate, and the solvent was distilled off under reduced pressure to give an oil, which gradually solidified. The comminuted solid was stirred with 100 parts by volume of methyl tert.-butyl ether at 50° C., filtered off under suction and freed from residual solvent under reduced pressure. 2-(Ethoxyaminobutylidene)-5-(5,6-dihydro-2H-1,1-dioxothiopyran-3-yl)-cyclohexane-1,3-dione was obtained as a solid of melting point 145°–148° C. (active ingredient no. 1).

The following compounds of the formula I can be obtained in a similar manner:

| Active ingredient no. | A | $R^1$ | $R^2$ | $R^3$ | $n_D$/m.p. [°C.] |
|---|---|---|---|---|---|
| 2 | 1,1-dioxotetrahydrothiopyran-3-yl | H | ethyl | ethyl | |
| 3 | 5,6-dihydro-2H—1,1-dioxothiopyran-3-yl | H | n-propyl | allyl | |
| 4 | 5,6-dihydro-2H—1,1-dioxothiopyran-3-yl | H | ethyl | ethyl | |
| 5 | 5,6-dihydro-2H—1,1-dioxothiopyran-3-yl | H | ethyl | allyl | |
| 6 | 5,6-dihydro-2H—1,1-dioxothiopyran-3-yl | H | ethyl | propargyl | |
| 7 | 5,6-dihydro-2H—1,1-dioxothiopyran-3-yl | H | ethyl | 3-chloroallyl | |
| 8 | 5,6-dihydro-2H—1,1-dioxothiopyran-3-yl | COOCH$_3$ | ethyl | ethyl | |
| 9 | 5,6-dihydro-2H—1,1-dioxothiopyran-3-yl | COOCH$_3$ | ethyl | allyl | |
| 10 | 5,6-dihydro-2H—1-oxothiopyran-3-yl | H | ethyl | allyl | |
| 11 | 5,6-dihydro-2H—1-oxothiopyran-3-yl | H | n-propyl | allyl | |
| 12 | 1-oxotetrahydrothiopyran-3-yl | H | n-propyl | allyl | |
| 13 | 1-oxotetrahydrothiopyran-3-yl | H | n-propyl | ethyl | |
| 14 | 1-oxotetrahydrothiopyran-3-yl | H | ethyl | ethyl | |
| 15 | 1-oxotetrahydrothiopyran-3-yl | H | ethyl | allyl | |
| 16 | 1,1-dioxotetrahydrothiopyran-3-yl | H | n-propyl | allyl | |
| 17 | 1,1-dioxotetrahydrothiopyran-3-yl | H | n-propyl | ethyl | |
| 18 | 2,6-dimethyl-1-oxotetrahydrothiopyran-3-yl | H | n-propyl | ethyl | |
| 19 | 2,6-dimethyl-1-oxotetrahydrothiopyran-3-yl | H | n-propyl | allyl | |
| 20 | 2,6-dimethyl-1,1-dioxotetrahydrothiopyran-3-yl | H | n-propyl | ethyl | |
| 21 | 2,6-dimethyl-1,1-dioxotetrahydrothiopyran-3-yl | H | n-propyl | allyl | |
| 22 | 2,6-dimethyl-5,6-dihydro-2H—1-1-oxo-thiopyran-3-yl | H | n-propyl | allyl | |
| 23 | 2,6-dimethyl-5,6-dihydro-2H—1-1-oxo-thiopyran-3-yl | H | n-propyl | ethyl | |
| 24 | 2,6-dimethyl-5,6-dihydro-2H—1,1-dioxothiopyran-3-yl | H | n-propyl | ethyl | |
| 25 | 2,6-dimethyl-5,6-dihydro-2H—1,1-dioxothiopyran-3-yl | H | n-propyl | allyl | |
| 26 | 1-oxotetrahydrothien-3-yl | H | n-propyl | allyl | |
| 27 | 1-oxotetrahydrothien-3-yl | H | n-propyl | ethyl | |
| 28 | 1,1-dioxotetrahydrothien-3-yl | H | n-propyl | ethyl | |
| 29 | 1,1-dioxotetrahydrothien-3-yl | H | n-propyl | allyl | |
| 30 | 2,5-dihydro-1-oxothien-3-yl | H | n-propyl | allyl | |
| 31 | 2,5-dihydro-1-oxothien-3-yl | H | n-propyl | ethyl | |
| 32 | 2,5-dihydro-1,1-dioxothien-3-yl | H | n-propyl | ethyl | |
| 33 | 2,5-dihydro-1,1-dioxothien-3-yl | H | n-propyl | allyl | |
| 34 | 2-methyl-1-oxotetrahydrothien-3-yl | H | n-propyl | allyl | |
| 35 | 2-methyl-1-oxotetrahydrothien-3-yl | H | n-propyl | ethyl | |
| 36 | 2,5-dihydro-2-methyl-1-oxothien-3-yl | H | n-propyl | ethyl | |
| 37 | 2,5-dihydro-2-methyl-1-oxothien-3-yl | H | n-propyl | allyl | |
| 38 | 2,5-dihydro-2-methyl-1,1-dioxothien-3-yl | H | n-propyl | allyl | |
| 39 | 2,5-dihydro-2-methyl-1,1-dioxothien-3-yl | H | n-propyl | ethyl | |
| 40 | 2,2-dimethyl-1-oxotetrahydrothien-3-yl | H | n-propyl | ethyl | |
| 41 | 2,2-dimethyl-1-oxotetrahydrothien-3-yl | H | n-propyl | allyl | |
| 42 | 2,2-dimethyl-1,1-dioxotetrahydrothien-3-yl | H | n-propyl | allyl | |
| 43 | 2,2-dimethyl-1,1-dioxotetrahydrothien-3-yl | H | n-propyl | ethyl | |
| 44 | 2,5-dihydro-2,2-dimethyl-1-oxothien-3-yl | H | n-propyl | ethyl | |
| 45 | 2,5-dihydro-2,2-dimethyl-1-oxothien-3-yl | H | n-propyl | allyl | |
| 46 | 2,5-dihydro-2,2-dimethyl-1-dioxothien-3-yl | H | n-propyl | allyl | |

-continued

| Active ingredient no. | A | R¹ | R² | R³ | $n_D$/m.p. [°C.] |
|---|---|---|---|---|---|
| 47 | 2,5-dihydro-2,2-dimethyl-1,1-dioxothien-3-yl | H | n-propyl | ethyl | |
| 48 | 2-methyl-2-(3-methyl-2-buten-1-yl)-1-oxo-tetrahydrothien-3-yl | H | n-propyl | ethyl | |
| 49 | 2-methyl-2-(3-methyl-2-buten-1-yl)-1-oxo-tetrahydrothien-3-yl | H | n-propyl | allyl | |
| 50 | 1,1-dioxo-2-methyl-2-(3-methyl-2-buten-1-yl)-tetrahydrothien-3-yl | H | n-propyl | allyl | |
| 51 | 1,1-dioxo-2-methyl-2-(3-methyl-2-buten-1-yl)-tetrahydrothien-3-yl | H | n-propyl | ethyl | |
| 52 | 2,5-dihydro-2-methyl-2-(3-methyl-2-buten-1-yl)-1-oxothien-3-yl | H | n-propyl | ethyl | |
| 53 | 2,5-dihydro-2-methyl-2-(3-methyl-2-buten-1-yl)-1-oxothien-3-yl | H | n-propyl | allyl | |
| 54 | 2,5-dihydro-1,1-dioxo-2-methyl-2-(3-methyl-2-buten-1-yl)-thien-3-yl | H | n-propyl | ethyl | |
| 55 | 2,5-dihydro-1,1-dioxo-2-methyl-2-(3-methyl-2-buten-1-yl)-thien-3-yl | H | n-propyl | allyl | |
| 56 | 4-methyl-1-oxotetrahydrothien-2-yl | H | n-propyl | allyl | |
| 57 | 4-methyl-1-oxotetrahydrothien-2-yl | H | n-propyl | ethyl | |
| 58 | 1,1-dioxo-4-methyltrahydrothien-2-yl | H | n-propyl | ethyl | |
| 59 | 1,1-dioxo-4-methyltrahydrothien-2-yl | H | n-propyl | allyl | |
| 60 | 2,5-dihydro-1,1-dioxo-4-methylthien-2-yl | H | n-propyl | allyl | |
| 61 | 2,5-dihydro-1,1-dioxo-4-methylthien-2-yl | H | n-propyl | ethyl | |
| 62 | 2,5-dihydro-4-methyl-1-oxo-thien-2-yl | H | n-propyl | ethyl | |
| 63 | 2,5-dihydro-4-methyl-1-oxo-thien-2-yl | H | n-propyl | allyl | |
| 64 | 1-oxotetrahydrothien-2-yl | H | n-propyl | allyl | |
| 65 | 1-oxotetrahydrothien-2-yl | H | n-propyl | ethyl | |
| 66 | 1,1-dioxotetrahydrothien-2-yl | H | n-propyl | ethyl | |
| 67 | 1,1-dioxotetrahydrothien-2-yl | H | n-propyl | allyl | |
| 68 | 2-methyl-1-oxo-1,3-dithiolan-2-yl | H | n-propyl | allyl | |
| 69 | 2-methyl-1-oxo-1,3-dithiolan-2-yl | H | n-propyl | ethyl | |
| 70 | 1,3-dioxo-2-methyl-1,3-dithiolan-2-yl | H | n-propyl | ethyl | |
| 71 | 1,3-dioxo-2-methyl-1,3-dithiolan-2-yl | H | n-propyl | allyl | |
| 72 | 2-methyl-1,1,3-trioxo-1,3-dithiolan-2-yl | H | n-propyl | allyl | |
| 73 | 2-methyl-1,1,3-trioxo-1,3-dithiolan-2-yl | H | n-propyl | ethyl | |
| 74 | 2-methyl-1,1,3,3-tetraoxo-1,3-dithiolan-2-yl | H | n-propyl | ethyl | |
| 75 | 2-methyl-1,1,3,3-tetraoxo-1,3-dithiolan-2-yl | H | n-propyl | allyl | |
| 76 | 1-oxotetrahydrothiopyran-3-yl | H | n-propyl | 3-chloroallyl | |
| 77 | 1-oxotetrahydrothiopyran-3-yl | H | n-propyl | propargyl | |
| 78 | 1-oxotetrahydrothiopyran-3-yl | H | ethyl | propargyl | |
| 79 | 1-oxotetrahydrothiopyran-3-yl | H | ethyl | 3-chloroallyl | |
| 80 | 1-oxotetrahydrothiopyran-3-yl | H | methyl | allyl | |
| 81 | 1-oxotetrahydrothiopyran-3-yl | H | methyl | ethyl | |
| 82 | 1,1-dioxotetrahydrothiopyran-3-yl | H | n-propyl | propargyl | |
| 83 | 1,1-dioxotetrahydrothiopyran-3-yl | H | n-propyl | 3-chloroallyl | |
| 84 | 1,1-dioxotetrahydrothiopyran-3-yl | H | ethyl | 3-chloroallyl | |
| 85 | 1,1-dioxotetrahydrothiopyran-3-yl | H | ethyl | propargyl | |
| 86 | 1,1-dioxotetrahydrothiopyran-3-yl | H | methyl | ethyl | |
| 87 | 1,1-dioxotetrahydrothiopyran-3-yl | H | methyl | allyl | |
| 88 | 5,6-dihydro-2H—oxothiopyran-3-yl | H | n-propyl | ethyl | |
| 89 | 5,6-dihydro-2H—oxothiopyran-3-yl | H | n-propyl | propargyl | |
| 90 | 5,6-dihydro-2H—oxothiopyran-3-yl | H | n-propyl | 3-chloroallyl | |
| 91 | 5,6-dihydro-2H—oxothiopyran-3-yl | H | ethyl | n-propyl | |
| 92 | 5,6-dihydro-2H—oxothiopyran-3-yl | H | methyl | ethyl | |
| 93 | 5,6-dihydro-2H—oxothiopyran-3-yl | H | methyl | allyl | |
| 94 | 5,6-dihydro-2H—oxothiopyran-3-yl | H | ethyl | ethyl | |
| 95 | 5,6-dihydro-2H—1,1-dioxothiopyran-3-yl | H | n-propyl | propargyl | |
| 96 | 5,6-dihydro-2H—1,1-dioxothiopyran-3-yl | H | n-propyl | 3-chloroallyl | |
| 97 | 5,6-dihydro-2H—1,1-dioxothiopyran-3-yl | H | ethyl | n-propyl | |
| 98 | 1-oxo-tetrahydrothiopyran-4-yl | H | n-propyl | ethyl | |
| 99 | 1-Oxo-tetrahydrothiopyran-4-yl | H | n-propyl | allyl | |
| 100 | 1,1-dioxotetrahydrothiopyran-4-yl | H | n-propyl | allyl | |
| 101 | 1,1-dioxotetrahydrothiopyran-4-yl | H | n-propyl | ethyl | |

The cyclohexane-1,3-dione derivatives of the formula I are identified by ¹H-NMR data:

| Compound no. | ¹H—NMR data [ppm], based on tetramethyl-silane as internal standard |
|---|---|
| 1 | 1.0 (t), 3.60 (s), 5.75 (s) |
| 2 | 1.15 (t), 1.32 (t), 2.20 (m), 4.10 (q) |
| 4 | 1.15 (t), 2.60 (s), 3.60 (s), 5.75 (s) |
| 5 | 0.97 (t), 3.80 (s), 4.55 (d), 5.70 (s) |
| 8 | 1.10 (t), 3.55 (s), 3.75 (s), 4.10 (q) |
| 9 | 1.15 (t), 3.78 (s), 4.55 (d) |
| 10 | 1.20 (t), 2.60 (m), 4.58 (d), 5.75 (s) |
| 13 | 0.97 (t), 1.32 (t), 4.15 (q) |
| 14 | 1.18 (t), 1.33 (t), 4.13 (q) |
| 17 | 1.00 (t), 2.15 (s), 4.15 (q) |
| 18 | 0.82 (t), 1.16 3.98 (q) |
| 20 | 0.85 (t), 1.70 (q), 4.05 (q) |
| 80 | 2.40 (s), 4.60 (d), 6.0 (m) |
| 81 | 1.33 (t), 2.40 (s), 3.48 (m) |
| 86 | 1.35 (t), 2.40 (s), 3.05 (m) |
| 87 | 2.40 (s), 2.55 (m), 4.68 (d) |
| 88 | 1.00 (t), 1.58 (q), 2.60 (m), 5.75 (s) |
| 89 | 0.98 (t), 1.58 (q), 2.58 (s), 4.78 (d) |

-continued

| Compound no. | $^1$H—NMR data [ppm], based on tetramethyl-silane as internal standard |
|---|---|
| 90 | 0.95 (t), 1.56 (q), 2.68 (m), 4.54 (d) |
| 91 | 1.20 (t), 1.80 (q), 2.60 (m) |
| 94 | 1.40 (t), 2.60 (m), 3.30 (m), 4.15 (q) |
| 95 | 0.95 (t), 2.52 (s), 3.55 (s), 4.67 (d) |
| 96 | 0.98 (t), 3.58 (s), 4.55 (d), 4.80 (d) |
| 97 | 3.15 (m), 3.76 (s), 3.95 (t), 5.70 (s) |

The cyclohexane-1,3-dione derivatives of the formula I are suitable for combatting grasses, and they also effect an increase in the carbohydrate content of the leaves of treated plants.

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 10 parts by weight of compound no. 2 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 13 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 14 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 88 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 17 is intimately mixed with 95 parts by weight of particulate kaolin. A dust is obtained containing 5% by weight of the active ingredient.

VII. 30 parts by weight of compound no. 88 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-ureaform-aldehyde condensate and 68 parts of a paraffinic mineral oil. A stable oily dispersion is obtained.

The active ingredients, or agents containing them, may be applied pre- or postemergence. If certain crop plants tolerate the active ingredients less well when they are applied postemergence, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, the type of soil and the application method employed, and varies from 0.025 to 3 kg/ha and more, but is preferably from 0.1 to 1.0 kg/ha.

The herbicidal action of the cyclohexane-1,3-dione derivatives of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 0.5 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. No covers were placed on the pots in this treatment method. The application rate was 0.125 kg of active ingredient per hectare.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Echinochloa crus-galli, Glycine max., Rottboellia exaltata, Setaria italica, Sorghum halepense, Bromus inermis, Digitaria sanguinalis,* and *Triticum aestivum.*

For example compound no. 1, both on pre- and postemergence application, exhibited a good herbicidal action on unwanted grasses. Soybeans, as an example of a broad-leaved crop, remained completely undamaged. Compounds nos. 2, 13, 14, 17 and 88, applied postemergence at a rate of 0.125 kg/ha, had a very good action on unwanted grass species; soybeans were not damaged by these compounds either.

In view of the numerous application methods possible the compounds according to the invention may be used in a further, large number of crops for removing unwanted wild grasses or grassy crop plants growing where they are not desired. The following crops may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. altisima | sugarbeets |
| *Beta vulgaris* spp. rapa | fodder beets |
| *Beta vulgaris* spp. esculenta | table beets, red beets |
| *Brassica napus* var. napus | rapeseed |
| *Brassica napus* var. napobrassica | |
| *Brassica napus* var. rapa | turnips |
| *Brassica rapa* var. silvestris | |
| *Camellia sinensis* | tea plants |
| *Carthamus tineterius* | stafflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plant |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helanthus annuus* | sunflowers |
| *Helanthus tuberosus* | |
| *Hevea brasiliensis* | rubber plants |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissmum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Ooea europaea* | olive trees |
| *Phaseolus lunatus* | limabeans |
| *Phaseolus mungo* | mungbeans |
| *Phaseolus vugaris* | snapbeans, green beans, dry beans |
| *Pennisetum glaucum* | |
| *Petroselinum crispum* spp. tuberosum | parsley |
| *Picea abies* | Norway spruce |
| *Abies alba* | fir trees |
| *Pins* spp. | pine trees |
| *Pisum sativum* | English peas |
| *Prunus avium* | cherry trees |
| *Prunus domestica* | plum trees |
| *Prunus dulcis* | almond trees |
| *Purnus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |

-continued

| Botanical name | Common name |
| --- | --- |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Vaccinium corymbosum | blueberries |
| Vaccinium vitis-idaea | canberries |
| Vicia faba | tick beans |
| Vigna sinensis (V. unguiculata) | cow peas |
| Vitis vinifera | grapes |

To increase the spectrum of action and to achieve synergistic effects, the cyclohexane-1,3-dione derivatives of the formula I, or agents containing them, may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, triazinones, uracils, benzofuran derivatives, other cyclohexane-1,3-dione derivatives, etc.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

We claim:

1. A cyclohexane-1,3-dione derivative of the formula

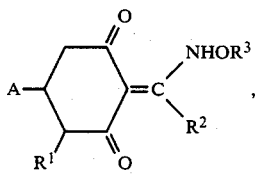

(I)

where A is a saturated or unsaturated 4-membered to 7-membered ring which contains 1 or 2 sulfinyl or sulfonyl groups and is unsubstituted or substituted by not more than 3 alkyl groups, each of not more than 4 carbon atoms, 2 alkenyl groups, each of not more than 6 carbon atoms, or 3 alkoxy groups, each of not more than 2 carbon atoms, $R^1$ is hydrogen, methoxycarbonyl, ethoxycarbonyl, methyl or cyano, $R^2$ is alkyl of 1 to 4 carbon atoms and $R^3$ is alkyl of 1 to 4 carbon atoms, alkenyl of 3 or 4 carbon atoms or haloalkenyl of 3 or 4 carbon atoms which has 1 to 3 halogen substituents, or is propargyl, or a salt thereof.

2. A cyclohexane-1,3-dione derivative of the formula I as defined in claim 1, where $R^1$ is hydrogen.

3. A cyclohexane-1,3-dione derivative of the formula I as defined in claim 1, where A is a saturated or unsaturated, 5- or 6-membered ring which contains 1 or 2 sulfinyl or sulfonyl groups and is unsubstituted or substituted by not more than 3 alkyl groups, each of not more than 4 carbon atoms, 2 alkenyl groups, each of not more than 6 carbon atoms, or 3 alkoxy groups, each of not more than 2 carbon atoms.

4. A cyclohexane-1,3-dione derivative of the formula I as defined in claim 1, where A is 5,6-dihydro-2H-1-oxothiopyran-3-yl, $R^1$ is hydrogen, $R^2$ is n-propyl, and $R^3$ is ethyl.

5. A herbicidal composition comprising inert additives and a herbicidally effective amount of cyclohexane-1,3-dione derivative of the formula I as defined in claim 1, or a salt of such a cyclohexane-1,3-dione derivative.

6. A herbicidal composition containing inert additives and from 0.1 to 95 wt% of a cyclohexane-1,3-dione derivatives of the formula I as defined in claim 1, or a salt of such a cyclohexane-1,3-dione derivative.

7. A herbicidal composition as defined in claim 5, where the cyclohexane-1,3-dione derivative of the formula I is one in which $R^1$ is hydrogen.

8. A herbicidal composition as defined in claim 5, where the cyclohexane-1,3-dione derivative of the formula is one in which A is a saturated or unsaturated, 5- or 6-membered ring which contains 1 or 2 sulfinyl or sulfonyl groups and is unsubstituted or substituted by not more than 3 alkyl groups, each of not more than 4 carbon atoms, 2 alkenyl groups, each of not more than 6 carbon atoms, or 3 alkoxy groups, each of not more than 2 carbon atoms.

9. A herbicidal composition as defined in claim 5, where the cyclohexane-1,3-dione derivative of the formula I is one in which A is 5,6-dihydro-2H-1-oxothiopyranyl, 1-oxotetrahydrothiopyranyl or 1,1-dioxotetrahydrothiopyranyl.

10. A process for combatting the growth of unwanted plants, wherein the unwanted plants and/or the area to be kept free from unwanted plant growth are treated with a herbicidally effective amount of a cyclohexane-1,3-dione derivative of the formula I as defined in claim 1, or a salt thereof.

11. A process as set forth in claim 10, wherein the unwanted plants are grasses.

* * * * *